United States Patent [19]

Poore et al.

[11] Patent Number: 5,423,869
[45] Date of Patent: Jun. 13, 1995

[54] MULTI-SENSOR RATE-RESPONSIVE PACEMAKER AND METHOD OF OPERATING SAME

[75] Inventors: John W. Poore, South Pasadena; Roy B. Medlin, West Hills, both of Calif.

[73] Assignee: Pacesetter, Inc., Sylmar, Calif.

[21] Appl. No.: 6,906

[22] Filed: Jan. 21, 1993

[51] Int. Cl.$^6$ ............................................ A61N 1/365
[52] U.S. Cl. .................................. 607/18; 607/19; 607/22
[58] Field of Search ................ 607/9, 2, 17, 18, 19, 607/22

[56] References Cited

U.S. PATENT DOCUMENTS

| | | | |
|---|---|---|---|
| 4,140,132 | 2/1979 | Dahl | 128/419 |
| 4,399,820 | 8/1983 | Wirtzfeld | 128/419 |
| 4,485,813 | 12/1984 | Anderson et al. | 128/675 |
| 4,712,555 | 12/1987 | Thornander et al. | 128/419 |
| 4,722,342 | 2/1988 | Amundson | 128/419 |
| 4,788,980 | 12/1988 | Mann et al. | 128/419 |
| 4,809,697 | 3/1989 | Causey et al. | 128/419 |
| 4,815,469 | 3/1989 | Cohen et al. | 128/634 |
| 4,867,161 | 9/1989 | Schaldach | 128/419 PG |
| 4,867,162 | 9/1989 | Schaldach | 128/419 PG |
| 4,867,163 | 9/1989 | Schaldach | 128/419 PG |
| 4,873,980 | 10/1989 | Schaldach | 128/419 |
| 4,940,052 | 7/1990 | Mann et al. | 128/419 |
| 4,944,298 | 7/1990 | Sholder | 128/419 |
| 5,097,831 | 3/1992 | Lekholm | 128/419 |

Primary Examiner—William E. Kamm
Assistant Examiner—Kennedy J. Schaetzle
Attorney, Agent, or Firm—Lisa P. Weinberg; Samuel M. Katz

[57] ABSTRACT

A rate-response pacemaker includes a plurality of sensors that each sense a physiologic-related parameter suggestive of the physiological needs of a patient, and hence indicative of the pacing rate at which the rate-responsive pacemaker should provide pacing pulses on demand. The pacemaker includes appropriate selection circuitry for selecting which of the sensor parameters or weighted combinations thereof, should be used as the sensor indicated rate (SIR) signal to control the pacing rate of the pacemaker at any given time. In a preferred embodiment, a maximum sensor rate signal ($MR_i$) is computed for each sensor, and a maximum sensor rate (MSR) signal is defined for the pacemaker, and the SIR signal is selected as the lesser of: (i) the MSR signal; (ii) the largest of the sensed sensor parameters; or (iii) the respective $MR_i$ signals.

17 Claims, 5 Drawing Sheets

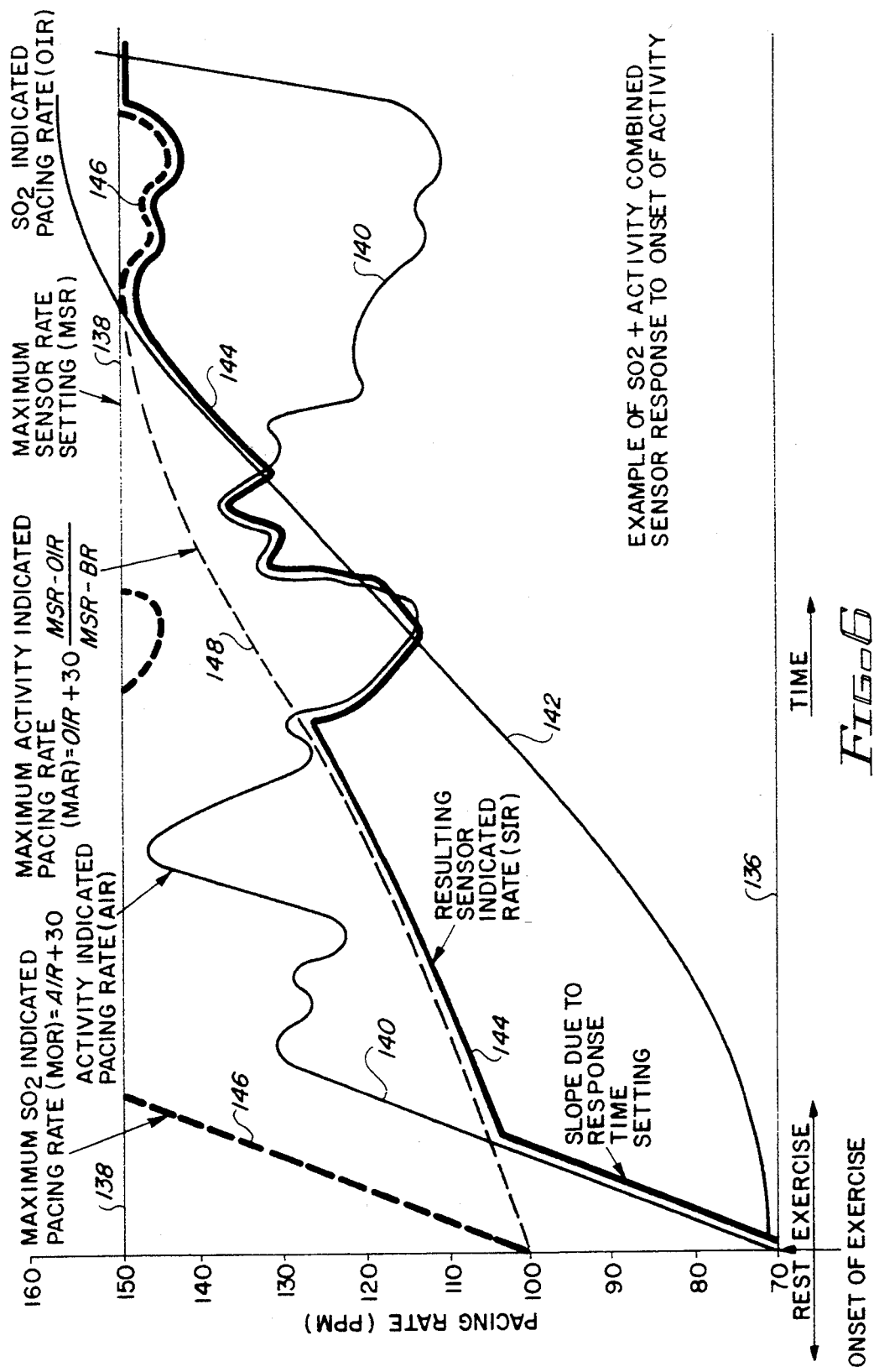

MULTI-SENSOR RATE-RESPONSIVE PACEMAKER AND METHOD OF OPERATING SAME

BACKGROUND OF THE INVENTION

Field of the Invention

The present invention relates to implantable medical devices and methods, and more particularly, to a rate-responsive pacemaker that includes a plurality of sensors for sensing a corresponding plurality of physiologic-related parameters indicative of an appropriate pacing rate. The invention also relates to a method of operating such a multi-sensor rate-responsive pacemaker to determine which of the plurality of physiologic-related parameters sensed by the plurality of sensors or which weighted combination thereof, should be selected to define the pacing rate of the pacemaker at any given time.

The heart is a pump that pumps life-sustaining blood through a patient's body in order to carry oxygen to, and remove carbon dioxide from, the tissue cells located throughout the body. In a healthy patient, i.e., a patient having a normal heart, the rate at which the blood is pumped through the body, which rate is determined by the heart rate, increases or decreases as the physiologic needs of the patient increase or decrease. That is, as the patient's body cells need more oxygen in order to do more work (as might occur, for example, if the patient starts to exercise), the heart rate increases in order to pump more blood, and hence more oxygen, to the cells. If insufficient oxygen is available (which oxygen is picked up by the blood in the lungs), then the respiration rate may also increase in order to increase the intake of oxygen. As the work being done by the patient's body is completed and as the demand for oxygen at the body cells decreases, then the heart rate slows, providing less blood flow, and hence less oxygen, to the cells. In this manner, the healthy heart maintains an optimum heart rate that keeps the body cells fed with a sufficient supply of oxygen to do whatever work they may be called upon to do. Supplying the body cells with the proper amount of oxygen by maintaining an adequate flow of blood, which flow dynamically increases and decreases as needed, is referred to generally as "hemodynamics."

A pacemaker is an implantable medical device that aids a patient with a diseased or damaged heart to maintain an adequate blood flow through his or her body. The pacemaker controls the rate at which the patient's heart beats, and thus controls the rate at which blood flows through the patient's body. To accomplish this function, the pacemaker includes sensing circuits that sense the natural heartbeat, e.g., the depolarization of the atria (as manifest by the occurrence of a P-wave) and/or the depolarization of the ventricles (as manifest by the occurrence of an R-wave or QRS complex). If a natural heartbeat is not sensed within a prescribed time interval since the last heartbeat, then a stimulation pulse (or "pacing pulse") is generated and delivered to the heart in order to stimulate the cardiac muscle tissue to contract. The prescribed time interval is typically referred to as the "escape interval." If a natural heartbeat is sensed before the escape interval times-out, then the escape interval is restarted, and no stimulation pulse is generated. In this way, the pacemaker provides stimulation pulses to the heart only when needed, i.e., only when a natural heartbeat does not occur during the escape interval. Providing stimulation pulses in this manner, i.e., only when needed, is referred to as providing stimulation pulses "on demand."

Most modern pacemakers allow the escape interval to be programmed to a desired value. Hence, the rate at which the pacing pulses are provided to the patient's heart can be programmed to a desired value. The rate at which pacing pulses are provided is typically referred to as the "pacing rate." So long as the natural heart rate of the patient exceeds the pacing rate, no stimulation pulses are generated by the pacemaker when the pacemaker is operating in a demand mode of operation (i.e., in a mode where stimulation pulses are provided on demand). However, as soon as the natural heart rate slows to a value below the pacing rate, the pacemaker generates whatever stimulation pulses are needed to maintain the heart rate at the pacing rate.

A rate-responsive pacemaker is a pacemaker that automatically adjusts the pacing rate as a function of a sensed physiologic-related parameter in order to achieve a hemodynamically beneficial pacing rate. Like conventional pacemakers, rate-responsive pacemakers provide pacing pulses to a patient's heart on demand (i.e., only when needed) in order to maintain the heart rate at the pacing rate. Unlike conventional pacemakers, a rate-responsive pacemaker includes a sensor that senses a physiologic-related parameter of the patient, e.g., physical activity, and adjusts the pacing rate within prescribed limits as a function of the sensed physiologic-related parameter. For example, suppose a patient has a rate-responsive pacemaker that uses an activity sensor, e.g., a piezoelectric crystal, to sense the physical activity of the patient. If the patient is at rest, the activity sensor fails to sense significant physical activity, and pacing pulses are provided on demand at a minimum rate, e.g, 70 pulses per minute (ppm), thereby assuring that the patient's heart rate is at least 70 beats per minute (bpm) (which rate is usually sufficient to meet the physiological demands of a patient at rest). If the patient is exercising, the activity sensor senses significant physical activity, and pacing pulses are provided on demand at a rate commensurate with the sensed physical activity, which rate may vary, e.g., from 70 ppm to 130 ppm, or higher. Thus, the heart rate of the patient, as controlled by the rate-responsive pacemaker, increases or decreases within prescribed limits as a function of the sensed physiologic-related parameter, thereby mimicking the hemodynamic response of a healthy heart in responding to changes in the physiological needs of the patient.

Rate-responsive pacemakers are known in the art that use a wide variety of physiologic-related sensors. See, e.g., U.S. Pat. Nos. 4,140,132 issued to Dahl (piezo activity sensor); U.S. Pat. No. 4,485,813 issued to Anderson et al. (piezo activity sensor); U.S. Pat. No. 4,712,555 issued to Thornander et al. (depolarization time interval); and U.S. Pat. No. 4,399,820 issued to Wirtzfeld et al. (blood oxygen sensor). Other types of physiologic-related sensors include body temperature sensors; blood Ph sensors; and respiration rate sensors. Note: as used herein, the term "physiologic-related sensor" refers to any sensor that senses a parameter that provides some indication of a change in the physiologic needs of a patient, whether the sensed parameter is a true physiological parameter or not. For example, the amount of oxygen in the blood is a true physiologic parameter. In contrast, the physical activity of a patient as sensed using a sensor that senses pressure on or acceleration of the pacemaker is not a true physiologic parameter. Nonetheless, physical activity sensed with such a sensor provides some indication or suggestion that the physiological needs of the patient may be changing.

Rate-responsive pacemakers are also known in the art that use a plurality of sensors and that then combine or otherwise process all of the outputs of the plurality of sensors in order to arrive at a single output that controls the rate at which the pacemaker provides stimulation pulses on demand. See, e.g, U.S. Pat. Nos. 4,722,342 issued to Amundson; and U.S. Pat. No. 5,097,831 issued to Lekholm. Such rate-responsive pacemakers using a plurality of sensors are referred to herein as multi-sensor rate-responsive pacemakers.

In a multi-sensor rate-responsive pacemaker, the relationship of the various sensor outputs to the pacing rate is typically a weighted combination of the sensor outputs. A function of the combination is then used to compute or to look up a corresponding pacing rate. The difficulty with this weighted combination approach is that the weighting of a given sensor output may have hemodynamic significance that varies with time and in relation to the magnitude of other sensor outputs. For example, consider a combination of sensors that includes an activity sensor (which typically measures movement or acceleration of, or pressure on, the pacemaker) and an oxygen sensor (which measures the saturated oxygen content of the blood and is referred to herein as an oxygen saturation sensor). Activity is measurable at the immediate onset of exercise or physical activity, whereas the oxygen saturation is not. Rather, the oxygen saturation has a latency associated therewith due to the transportation time of oxygen depleted blood from the muscle cells demanding more oxygen and the heart wherein the oxygen saturation sensor is typically located. Activity, although immediately available, is prone to false positive responses because it is not a physiologic parameter of the body. The oxygen saturation measurement, on the other hand, not being immediately available because of the above-described latency, is a true physiologic parameter that is directly related to the heart rate except for the latency. Thus, without factoring in the latency of the oxygen saturation measurement, there is no way to correctly weight the combination of the activity measurement and the oxygen saturation measurement. Hence, what is needed is a dynamic weighting approach wherein the sensed activity is more heavily weighted during the onset or acceleration of such sensed activity, and the sensed oxygen saturation is more heavily weighted during intervals of more stable sensed activity or at other times when the oxygen saturation parameter provides a better indication of the needed heart rate. More generally, what is needed for a multi-sensor rate-responsive pacemaker is a dynamic weighting or selection criteria wherein the sensor output that best represents the true physiologic needs of the patient at a given time is selected or weighted more heavily at such given time and is not-selected or lightly weighted during other times, thereby achieving a more hemodynamically beneficial pacing rate.

SUMMARY OF THE INVENTION

The above and other needs are met by the present invention wherein there is provided a rate-response pacemaker that includes a plurality of sensors for sensing a plurality of sensor parameters suggestive of the physiological needs of a patient and hence indicative of the pacing rate at which the rate-responsive pacemaker should provide pacing pulses on demand. More particularly, the invention provides specific selection circuitry and specific selection criteria for determining which of the plurality of sensor parameters, or which combinations thereof, should be used to control the pacing rate of the pacemaker at any given time so as to achieve a more hemodynamically beneficial pacing rate.

In accordance with one aspect of the invention, a weighted combination of a plurality of sensor signals is automatically selected as the pacemaker's sensor indicated rate (SIR) signal. The amount of weighting given one sensor signal at any given time varies as a function of which sensor signal best typifies the physiologic need of the patient at that time.

In accordance with another aspect of the invention, two different types of sensors are used by the multi-sensor rate-responsive pacemaker, and special selection circuitry selects which of the sensor signals, or combinations thereof, is to be used by the pacemaker to define the pacemaker's SIR signal. A first sensor is an oxygen saturation sensor and is used to measure the oxygen saturation level of the patient's blood. A second sensor is an activity sensor and is used to measure the physical activity level of the patient. The SIR signal generated by the selection circuitry comprises a weighted combination of the oxygen saturation sensor signal and the activity sensor signal, with the activity sensor signal being heavily weighted during the initial onset or acceleration of increased physical activity (e.g., exercise), and with the oxygen saturation sensor signal being heavily weighted at other times (e.g., rest, stable physical activity, or return to rest). In this way, the inherent latency in the oxygen saturation sensor signal (due to the transportation time of oxygen depleted blood from the muscles demanding more oxygen to the heart) is overridden with the activity sensor signal (which responds to the immediate onset of exercise). Thus, the pacing rate computed as a result of sensed activity only is slowly forced to converge with the pacing rate computed as a result of oxygen saturation only, with the optimal rate of such convergence being matched to the latency of the oxygen saturation measurement.

One embodiment of the invention may thus be characterized as an implantable rate-responsive pacemaker that includes: (1) a plurality of sensors, each being adapted to sense a physiologic-related parameter of a patient and to generate a sensor signal indicative of such sensed physiologic-related parameter; (2) a sense amplifier that senses natural contractions of the patient's heart; (3) a pulse generator that generates stimulation pulses responsive to a pacing signal, each stimulation pulse having a pacing energy sufficient to force a depolarization, and hence contraction, of a selected chamber of the patient's heart; (4) timing circuitry that defines an escape time interval; and (5) control logic that starts the escape time interval at the beginning of a sensed or paced cardiac cycle, and that generates the pacing signal at the end of the escape time interval unless a natural contraction of the patient's heart is sensed by the sense amplifier prior to the end of the escape interval, in which case the escape time interval is restarted and no pacing signal is generated. Such rate-responsive implantable pacemaker also includes processing means coupled to the timing circuitry for generating a sensor indicated rate (SIR) signal. The SIR signal is used by the timing means to define the duration of the escape time interval and is determined as a prescribed weighted combination of the plurality of sensor signals, with the amount of weighting given one sensor signal at any given time varying as a function of which sensor signal best typifies the physiologic need of the patient at that time.

A further embodiment of the invention may be characterized as an implantable rate-responsive pacing system. Such a pacing system includes a plurality of sensors, each being adapted to sense a respective physiologic-related parameter of a patient and to generate a physiological signal indicative of such sensed physiologic-related parameter. Such pacing system further includes a sense amplifier that senses natural contractions of the patient's heart; and pulse generator means for generating stimulation pulses responsive to a pacing signal and delivering the stimulation pulses to the patient's heart. Still further, the pacing system includes control/timing means for defining an escape interval and starting the escape interval at the beginning of a sensed or paced cardiac cycle, and generating the pacing signal at the end of the escape interval unless a natural contraction of the patient's heart is sensed by the sense amplifier prior to the conclusion of the escape interval, in which case the escape interval is restarted and no pacing signal is generated. The pacing system additionally includes telemetry means for programming the pacemaker with a desired base rate (BR) and a maximum sensor rate (MSR). Finally, the pacing system includes sensor processing means coupled to the control/timing means for generating a sensor indicated rate (SIR) signal. Such SIR signal is used by the control/timing means to define the duration of the escape interval. The SIR signal comprises the lesser of: (a) the MSR signal; or (b) the largest of the plurality of physiological signals. In this manner, the pacing system generates stimulation pulses on demand at a rate determined by the SIR signal so as to achieve a more hemodynamically beneficial pacing rate.

Still further, the invention may be characterized as a method of operating an implantable rate-responsive pacemaker that utilizes a plurality of rate sensors. Each of the rate sensors generates a respective rate signal that indicates a sensed physiologic-related parameter of a patient. The method comprises the steps of: (a) processing the plurality of rate signals to determine a sensor indicated rate (SIR) signal, where such processing includes: (1) defining a maximum sensor rate (MSR) signal, and (2) selecting the SIR signal as the lesser of: (i) the MSR signal, or (ii) the largest of the plurality of rate signals; (b) using the SIR signal to define an escape interval for the implantable rate-responsive pacemaker; (c) sensing natural cardiac activity of the patient; (d) starting the escape interval upon sensing natural cardiac activity; and (e) generating a stimulation pulse at the end of the escape interval and restarting the escape interval unless a natural contraction of the patient's heart is sensed prior to the end of the escape interval, in which case the escape interval is immediately restarted and no stimulation signal is generated. Thus, in this manner, the rate-responsive pacemaker generates stimulation pulses on demand at a rate determined by the SIR signal, where the SIR signal results from the specified processing of the plurality of rate signals obtained from the plurality of rate sensors.

It is thus a feature of the present invention to provide a rate-responsive pacemaker that uses signals from a plurality of sensors to determine the sensor indicated rate (SIR) signal used by the pacemaker for its rate-responsive functions so as to achieve a more hemodynamically beneficial pacing rate.

It is another feature of the invention to provide a multi-sensor rate-responsive pacemaker wherein a weighted combination of a plurality of sensor signals is automatically selected as the pacemaker's SIR signal, and wherein the amount of weighting given one sensor signal at any given time varies as a function of which sensor signal best typifies the physiologic need of the patient at that time.

It is an additional feature of the invention to provide a multi-sensor rate-responsive pacemaker using both an oxygen saturation sensor (to measure the oxygen saturation level of the patient's blood) and an activity sensor (to measure the physical activity level of the patient), and to select an SIR signal that is a weighted combination of the oxygen saturation sensor signal and the activity sensor signal, with the activity sensor signal being heavily weighted during the initial onset or acceleration of increased physical activity (e.g., exercise), and with the oxygen saturation sensor signal being heavily weighted at other times (e.g., rest, stable physical activity, or return to rest).

It is a further feature of the invention to provide such a multi-sensor rate-responsive pacemaker using both an oxygen saturation sensor and an activity sensor wherein one of: (a) the oxygen saturation sensor signal; (b) the activity sensor signal; (c) a predetermined (e.g., programmed) maximum sensor rate (MSR) signal; (d) a maximum oxygen saturation sensor rate (MOR) signal derived from the activity sensor signal; or (e) a maximum activity sensor rate (MAR) signal derived from the oxygen saturation sensor signal and other rate limits, is selected as the SIR signal used by the pacemaker for its rate-responsive functions. In one particular embodiment of such a multi-sensor rate-responsive pacemaker, it is a feature of the invention to select the SIR signal as the lesser of: (i) the MSR signal; (ii) the largest of the activity sensor signal or the oxygen saturation signal; (iii) the MOR signal; or (iv) the MAR signal.

BRIEF DESCRIPTION OF THE DRAWINGS

The above and other aspects, features and advantages of the present invention will be more apparent from the Detailed Description of the Invention presented in conjunction with the following drawings, wherein:

FIG. 6 shows a plot of the SIR signal as in FIG. 5 for a preferred embodiment of the invention using an oxygen saturation sensor and activity sensor, and further using a prescribed sensor-signal selection criteria.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is to be emphasized that the present invention relates to an implantable rate-responsive pacemaker that uses a plurality of sensors to sense a corresponding plurality of physiologic-related parameters. Each of the sensors generates a raw sensor signal that can be appropriately processed to derive a sensor indicated rate (SIR) signal for use by the pacemaker in determining its pacing rate, i.e., the rate at which it provides pacing pulses on demand to a patient's heart. The rate-responsive pacemaker of the present invention may be either a dual-chamber pacemaker or a single-chamber pacemaker, although the invention as described in FIGS. 1 and 2 below is a dual-chamber pacemaker. The invention described herein focuses primarily on the selection circuitry used by the invention to select an appropriate one or an appropriate weighted combination, of the plurality of raw sensor signals as the controlling sensor signal for the rate-responsive pacemaker. An overview of the basic operation of a rate-responsive pacemaker is first presented.

Figure 1:
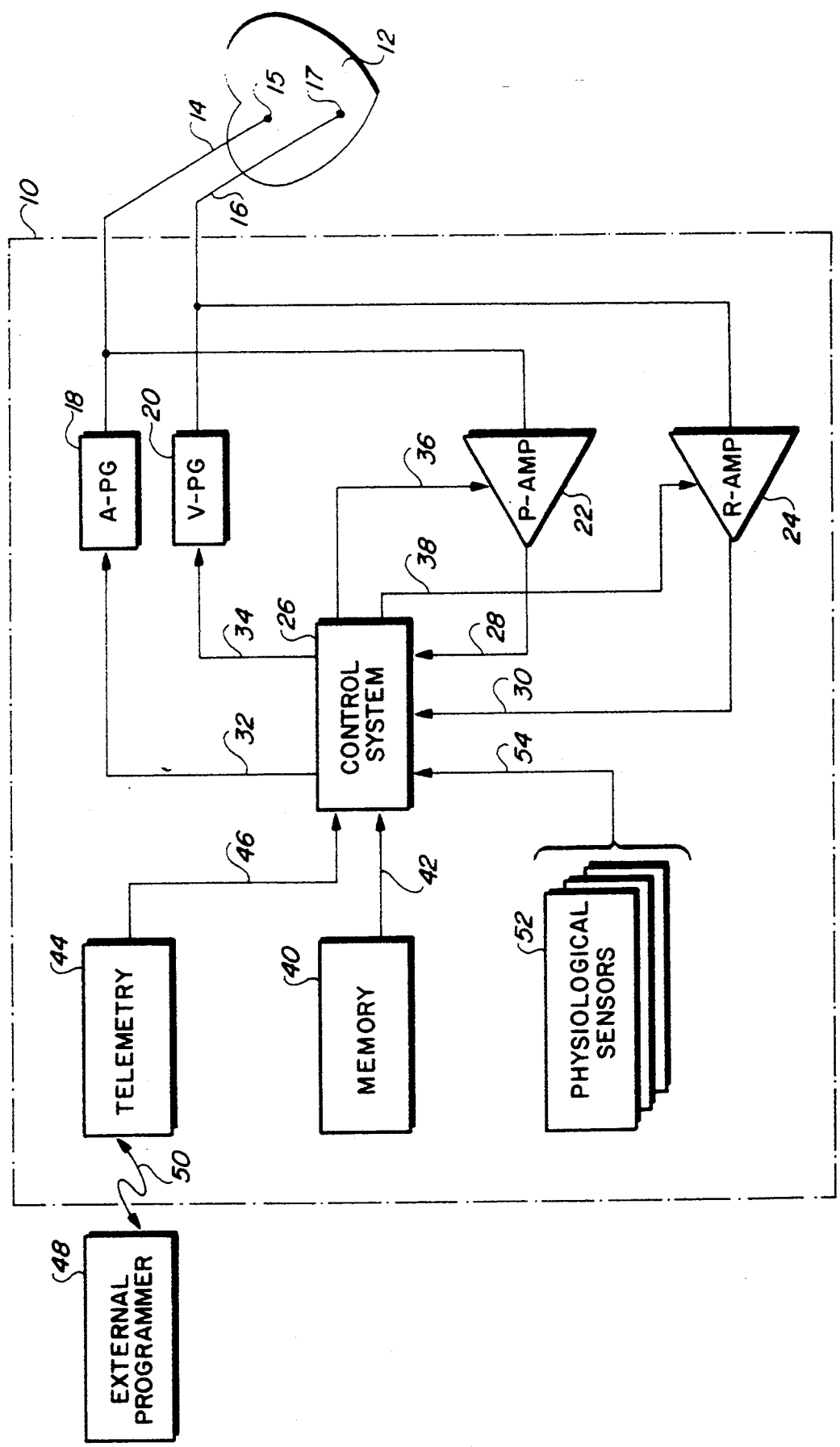
FIG. 1 shows a functional block diagram of a multi-sensor rate-responsive pacemaker made in accordance with the present invention.

Referring then to FIG. 1, a simplified block diagram of a dual-chamber pacemaker 10 is illustrated. A dual-chamber pacemaker is only illustrative of one type of pacemaker with which the present invention may be used. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacemaker 10 is a timing/control system 26. The timing/control system 26 (referred to hereafter as simply the control system 26) receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. The atrial trigger signal is referred to simply as the "A-pulse," and the ventricular trigger signal is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

Still referring to FIG. 1, the pacemaker 10 includes a memory circuit 40 that is coupled to the control system 26 over a suitable data/address bus 42. This memory circuit allows certain control parameters used by the control system 26 in controlling the operation of the pacemaker to be programmably stored and modified, as required, in order to customize the pacemaker's operation to suit the needs of a particular patient. Such parameters include the basic timing intervals used during operation of the pacemaker, such as the programmed escape interval (EI). Further, sensor signals or other signals sensed during the operation of the pacemaker may be stored in the memory 40 for later retrieval and analysis.

A telemetry circuit 44 is further included in the pacemaker 10. This telemetry circuit 44 is connected to the control system 26 by way of a suitable command/data bus 46. In turn, the telemetry circuit 44 which is included within the implantable pacemaker 10 may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacemaker 10. In this manner, noninvasive communications can be established with the implanted pacemaker 10 from a remote, non-implanted location.

The pacemaker 10 in FIG. 1 is referred to as a dual-chamber pacemaker because it interfaces with both the atria and the ventricles of the heart. Those portions of the pacemaker 10 that interface with the atria, e.g., the lead 14, the P-wave sense amplifier 22, the A-pulse generator 18, and corresponding portions of the control system 26, are commonly referred to as the atrial channel. Similarly, those portions of the pacemaker 10 that interface with the ventricles, e.g., the lead 16, the R-wave sense amplifier 24, the V-pulse generator 20, and corresponding portions of the control system 26, are commonly referred to as the ventricular channel. A single-chamber pacemaker, in contrast, has only an atrial channel or a ventricular channel. Most dual-chamber pacemakers can be programmed to operate in a single-chamber mode of operation.

In accordance with the present invention, the pacemaker 10 further includes a plurality of physiologic sensors 52 that is connected to the control system 26 of the pacemaker over a suitable connection line 54. While these sensors 52 are illustrated in FIG. 1 as being included within the pacemaker 10, it is to be understood that at least some of the sensors will likely be external to the pacemaker 10, yet still be implanted within or carried by the patient. A common type of sensor is an activity sensor, such as a piezoelectric crystal, mounted to the case of the pacemaker. Other types of physiologic sensors that may be included in the plurality of sensors 52 include sensors that sense the oxygen content of blood; respiration rate; pH of blood; body motion; the depolarization time interval; the repolarization time interval; and the like. The type of sensors used is not critical to the present invention. What is critical, is that there be at least two sensors. Any combination of two or more sensors, each capable of sensing some physiologic-related parameter that suggests the rate at which the heart should be beating can be used. A preferred sensor combination for the present invention is an activity sensor and an oxygen saturation sensor.

The sensors 52 are used with the rate-responsive pacemaker 10 in order to adjust the rate (escape interval) of the pacemaker in a manner that tracks the physiological needs of the patient. The manner in which the plurality of raw sensor signals are selected and processed in order to achieve this goal—of having the pacemaker track the physiological needs of the patient—is the primary thrust of this invention. Once the appropriate sensor signal or weighted combination of a plurality of sensor signals, has been selected or generated, such selected signal may then be processed by the rate-responsive pacemaker in conventional manner, as taught, e.g., in U.S. Pat. Nos. 4,712,555; 4,809,697; 4,940,052; or 4,940,053; which patents are incorporated herein by reference. Further processing of the sensor parameters of a rate-responsive pacemaker is disclosed in U.S. patent application Ser. No. 07/844,818, filed Mar. 2, 1992, entitled "Method and System for Automatically Adjusting the Sensor Parameters of a Rate-Responsive Pacemaker," assigned to the same assignee as the present invention, also incorporated herein by reference.

Figure 2:
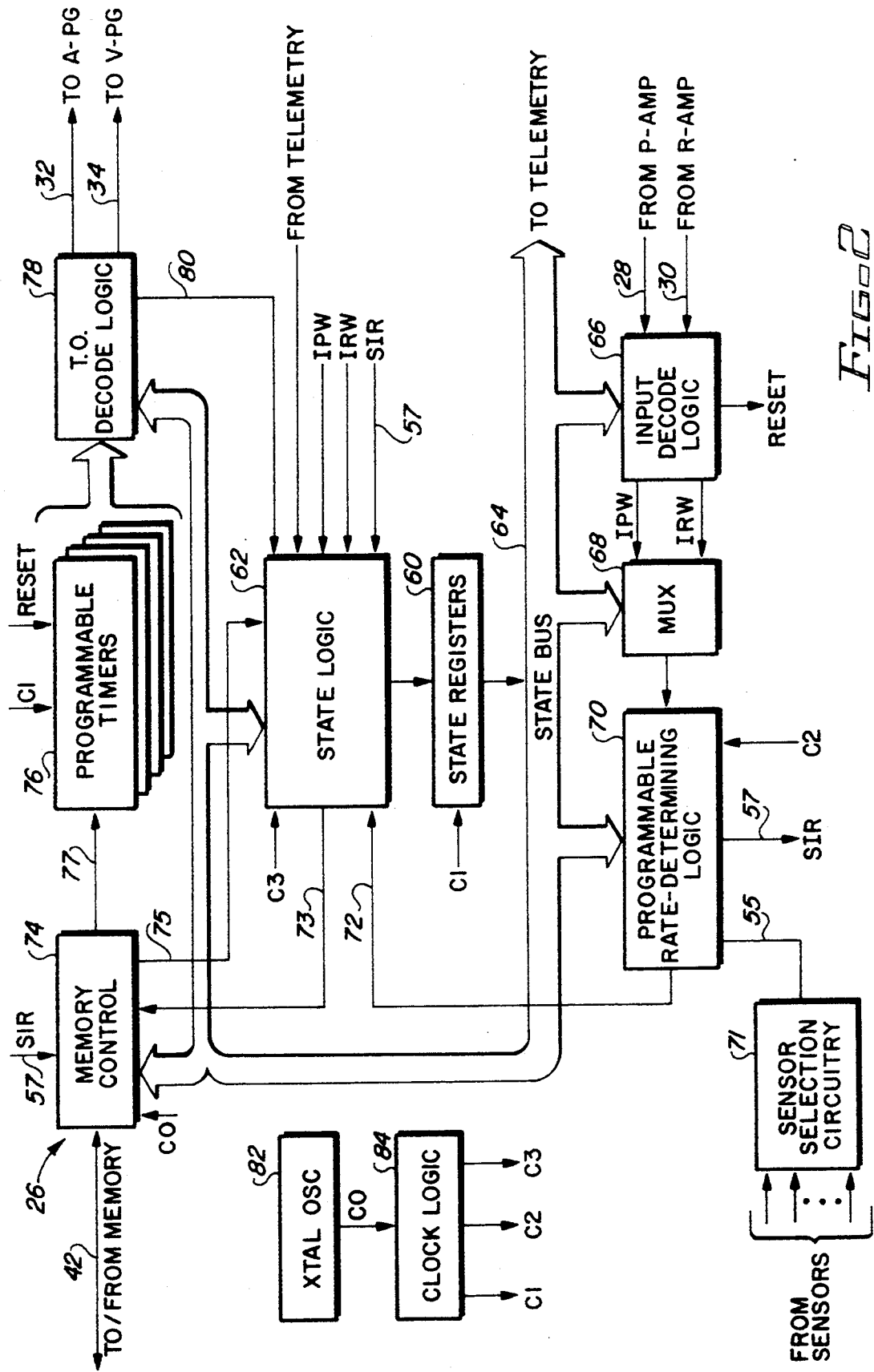
FIG. 2 is a functional block diagram of the control system of FIG. 1.

Referring next to FIG. 2, a block diagram of one embodiment of the control system 26 of the pacemaker 10 of FIG. 1 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment," previously incorporated herein by reference.

The control system shown in FIG. 2 is based on a state machine wherein a set of state registers 60 define the particular state of the pacemaker at any instant in time. In general and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. This telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (inhibiting P-wave) and "IRW" (inhibiting R-wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72.

Rate-determining logic 70 further receives a selected sensor signal from the sensor selection circuitry 71 over signal line 55. Depending upon the particular state of the system, as defined by the state registers 60, and as made available to the rate-determining logic 70 over the state bus 64, this selected sensor signal becomes an appropriate sensor indicated rate (SIR) signal. The SIR signal is then sent to the state logic 62 and/or to a memory control circuit 74 over signal line 57, where it is used to set the pacing rate (e.g., to define the appropriate escape interval) of the pacemaker.

Still referring to FIG. 2, the memory control circuit 74 provides the needed interface between the circuits of the control system 26, the memory 40 (FIG. 1), or the SIR signal. This memory control circuit is a conventional memory access circuit that sends or receives data to or from memory at a specified address. Data retrieved from memory 40 may be sent to either the state logic 62 (over signal line(s) 75) or to one or more programmable timers 76 (over signal line(s) 77). Data sent to memory 40 may be either the current state of the system (obtained off of the state bus 64); the SIR signal (which may be stored in a histogram, or the like); or other selected signals from the state logic (as made available over signal line(s) 73).

The programmable timers 76 define one or more prescribed time intervals, the length of which is set by the signal(s) received from the memory control 74 over signal line(s) 77. The starting point for a given time interval begins coincident with the start of the current state, as obtained from the state bus 64. The timers 76 further generate respective time-out (T.O.) signals when the prescribed time interval has elapsed. During a given prescribed time interval, the timing function may be reset by a reset signal, typically obtained from the input decode logic 66, although some states (as obtained from the state bus 64) may also effectuate an immediate reset of one or more of the timers 76. The time-out signals are sent to time-out decode logic 78. It is the function of the time-out decode logic to generate the appropriate trigger signals that are sent to the A-pulse generator 18 or the V-pulse generator 20 (FIG. 1) over signal lines 32 and 34, respectively. Further, an appropriate logic signal(s) is sent to the state logic 62 by the time-out decode logic 78 over signal line(s) 80 in order to notify the state logic that the respective trigger signals have been generated.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 kHz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 2 thus starts at an initial state, wherein the state registers 60 assume a prescribed value that defines the initial state. For example, assuming four flip-flops are used for the state registers 60, an initial state might be "1000" (hexadecimal "8") wherein the first flip-flop assumes a "1" state and the remaining three flip-flops each assume a "0" state. This state may be defined as a V-A delay (VAD) state wherein a prescribed ventricular-to-atrial (V-A) interval is initiated. This V-A interval may be considered as the "atrial escape interval," or "AEI." As soon as the memory control 74 detects that the AD state has been initiated, as evidenced by the "1000" appearing on the state bus 64, it retrieves from the memory 40 an appropriate data word, previously programmed into the memory 40 from the external programmer 48, that defines the desired length of the AEI; or, when operating in a rate-responsive mode, it retrieves the SIR signal (or a signal derived from the SIR signal) as such AEI-defining data word. The AEI data word is sent to one of the programmable timers 76 and sets the length of the time period that is to be measured during the AD state.

The timers 76 are essentially just counters that count down (or count up), using a specified clock signal, to the value specified in the data word. When the counting has been completed and assuming that a given counter has not been reset by the occurrence of a P-wave, the given one of the counters or timers 76 is said to have "timed-out," and an appropriate time-out signal is generated that is sent to the time-out decode logic 78 over line(s) 999. The decode logic, in turn, recognizes that the current state of the system is the VAD state (as determined by monitoring the state bus 64), and therefore that the AEI has timed-out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78 and also in response to the current AD state, triggers the next state of the prescribed sequence. For DDD operation, this state is typically a blanking state, or BLANK state, during which the P and R sense amplifiers 22 and 24 are disabled. Accordingly, the state logic generates appropriate signal(s) on signal lines 36 and 38 to blank the P-wave sense amplifier 22 and the R-wave sense amplifier 24 of FIG. 1 and also causes the state registers 60 to change to a BLANK state, which state could be defined, for example, by the flip-flops of the state registers 62 assuming a "0001" (hex "1") condition. This BLANK state detected on the state bus 64 causes the memory control circuitry to retrieve an appropriate data word from memory that defines the length of the blanking interval, which data word is loaded into one of the programmable timers 76. As soon as the timer 76 times-out, indicating that the prescribed blanking interval has elapsed, a time-out signal is generated that is sent to the time-out decode logic 78. Upon receipt of this time-out signal and in response to the current state being a BLANK state, the time-out decode logic 78 sends an appropriate logic signal to the state logic 62. The state logic 62 responds by steering the state registers 60 to assume the next state in the prescribed sequence, which may be, for example, an A-V delay state.

At the beginning of the A-V delay state, another value is loaded into an appropriate one of the programmable timers 76 that defines the length of the A-V delay, or "AVD." If the AVD timer times-out without being reset, indicating that no R-wave has been sensed, the decode logic generates a V-pulse trigger signal and notifies the state logic 62 of this event. The state logic, in turn, causes the next appropriate state to be entered, which state may be another blanking state or BLANK state, similar to the one described above, but having perhaps a different duration. At the conclusion or timing-out of this second BLANK state, the next state in the prescribed sequence is initiated, which state may be a refractory (REF) state.

In the manner described above, the control system 26 assumes one state after another, thereby controlling the operation of the pacemaker. In general, a state is changed when a specified one of the timers 76 times-out or when a prescribed event occurs.

It is noted that the state of the control system could also be changed by receipt of an appropriate command from the telemetry system.

The control system 26 of FIG. 1 may be realized using dedicated hardware circuits, or by using a combination of hardware and software (or firmware) circuits. The appropriate sequence of states for a given mode of operation, such as DDD or DI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 11 is not presented herein because all such circuits are conventional or may be patterned after known circuits available in the art. Reference is made, for example, to U.S. Pat. No. 4,712,555, wherein a state machine-type of operation for a pacemaker is described; U.S. Pat. No. 4,788,980, wherein the various timing intervals used within the pacemaker and their interrelationship are more thoroughly described; and U.S. Pat. No. 4,944,298, wherein an atrial rate-based programmable pacemaker is described, including a thorough description of the operation of the state logic used to control such a pacemaker. The '555 and '980 patents have previously been incorporated herein by reference. The '298 patent is also incorporated herein by reference.

Figure 3:
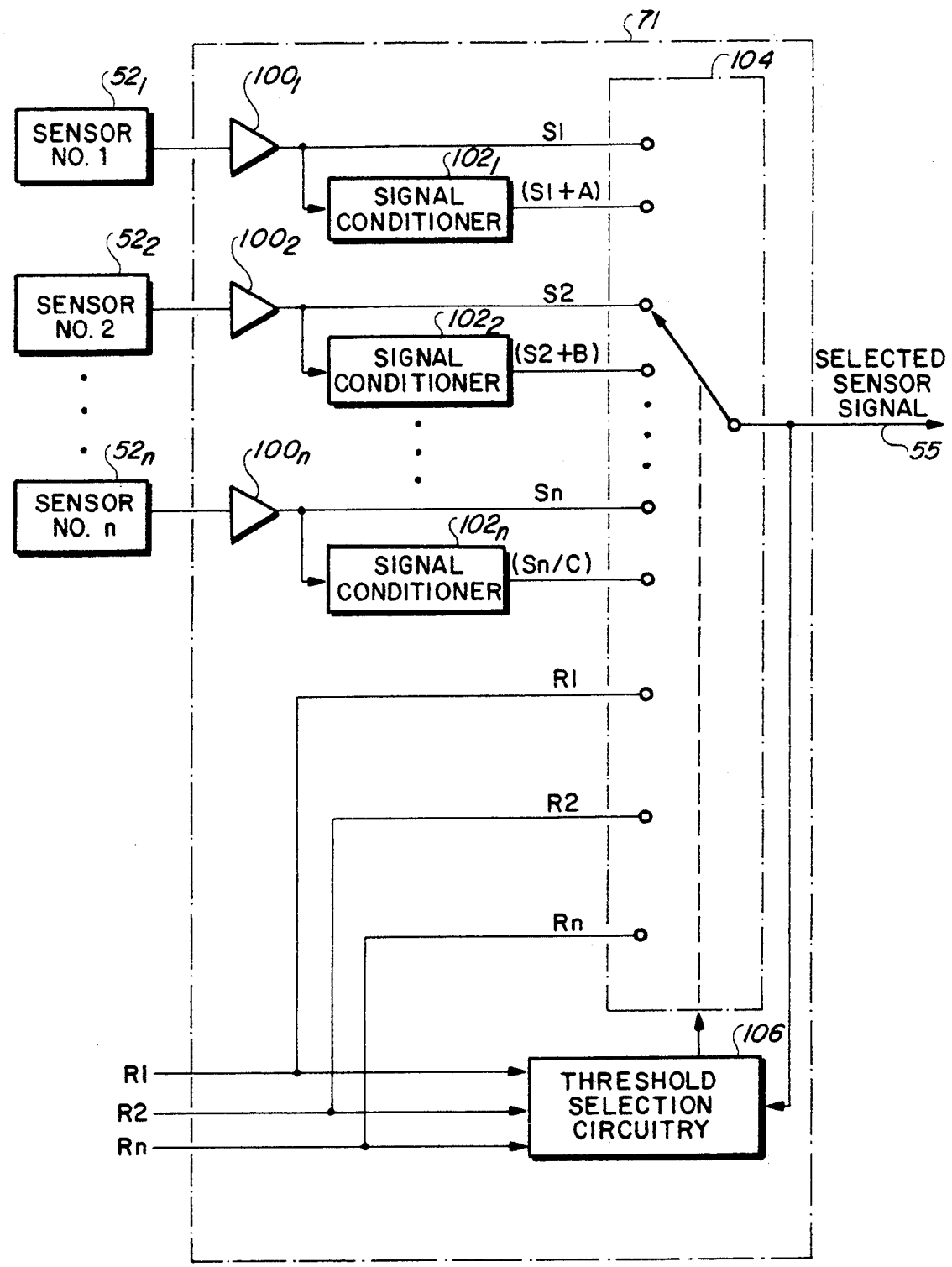
FIG. 3 is a functional block diagram of the sensor selection circuitry used within the control system of FIG. 2.

Of particular significance to the present invention is the sensor selection circuitry 71. A functional block diagram of the sensor selection circuitry 71 is shown in FIG. 3. As seen in FIG. 3, a plurality of sensors $52_1$, $52_2$, ... $52_n$ each generate a raw sensor signal as a function of a sensed physiologic-related parameter of the patient, e.g., physical activity, blood oxygen saturation, blood pH, respiration rate, and the like. Such raw sensor signals are received and amplified in respective buffer/amplifier circuits $100_1$, $100_2$, ... $100_n$. The output signals of the buffer/amplifier circuits are designated as the sensor signals S1, S2, ... Sn. Such signals thus provide an indication of the respective sensed physiologic-parameter. The sensor signals may comprise samples of the sensed physiologic-related parameters, or continuous signals of the sensed physiologic-related parameters. In general, then, each of the sensor signals S1, S2, ... Sn will vary over time as the particular sensed physiologic-related parameter varies with the changing physiological needs of the patient.

Included in the selection circuitry 71 are respective signal conditioning circuits $102_1$, $102_2$, ... $102_n$ for each of the sensor signals S1, S2, ... Sn. Each signal conditioning circuit $102_1$, $102_2$, ... $102_n$ processes its respective sensor signal in a prescribed manner. As shown in FIG. 3, for example, signal conditioner $102_1$ adds a fixed increment A to the sensor signal S1. Similarly, signal conditioner $102_2$ multiplies the sensor signal S2 by a prescribed factor B; and signal conditioner $102_n$ divides the sensor signal Sn by a specified factor C. Such processing steps are only exemplary, as any desired processing of the sensor signal may be carried out. Further, for some types of sensors, no additional processing, and hence no signal conditioner, may be needed. Moreover, even though FIG. 3 shows a separate signal conditioner associated with each sensor, it is to be understood that there may not be a separate signal conditioner for each sensor. Rather, a single signal conditioner may be used to process all of the sensor signals that are to be processed.

The sensor signals S1, S2, ... Sn, or the processed signals derived from the sensor signals S1, S2, ... Sn, in combination with a plurality of threshold reference signals R1, R2, ... Rn (which threshold reference signals are typically programmed values, but may also comprise a timed variable, e.g., a value that increases or decreases in a prescribed manner as a function of time), are then presented as inputs to a multiplexer circuit 104, or equivalent. The multiplexer circuit 104 functions as a switch, selecting one of its inputs as the selected sensor signal for delivery to the rate-determining logic 70 (FIG. 2) over signal line 55. Control of the multiplexer 104 is obtained from threshold selection circuitry 106. The threshold selection circuitry 106 monitors the threshold reference signals R1, R2, ... Rn, as well as the currently selected sensor signal on the output of the multiplexer 104 and selects the next sensor signal, or conditioned sensor signal, or threshold reference signal in accordance with a prescribed selection criteria.

By way of example only, the threshold selection circuitry may select the sensor signal S1 as the selected sensor signal for so long as S1 remains less than or equal to the threshold reference signal R1. However, as soon as S1 is greater than the threshold reference signal R1, then R1 is selected as the selected sensor signal if the sensor signal S2 is less than R1. If S2 is not less than R1, then S2 is selected as the selected sensor signal if S2 is less than the threshold reference signal R2. However, once S2 is equal to or greater than R2, then R2 is selected as the selected sensor signal if the sensor signal S3 is less than R2. Should S3 not be less than R2, then R2 is selected as the selected sensor signal.

The above-described exemplary selection criteria may be further modified by comparing the conditioned sensor signals to various ones of the threshold reference signals or sensor signals and changing the selected sensor signal when specified criteria are met.

In the above-described manner, the selected sensor signal, at any instant of time, comprises one of the sensor signals, conditioned sensor signals, or threshold reference signals as a function of a specified selection criteria. The specified selection criteria, in turn, is dependent upon the relative magnitudes of the sensor signals, conditioned sensor signals, and threshold reference signals.

Figure 4:
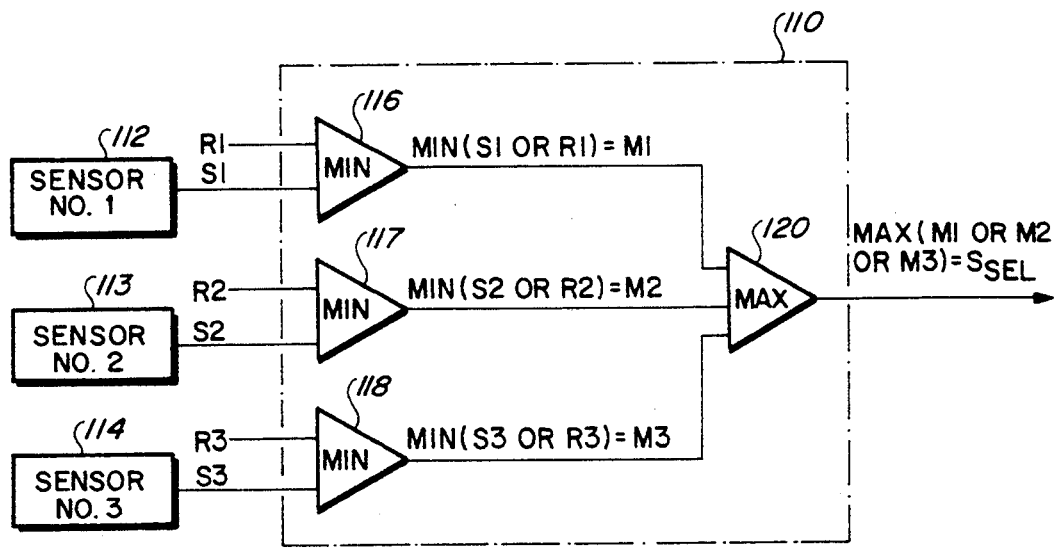
FIG. 4 shows a schematic diagram of threshold and logic circuitry that performs a prescribed sensor-signal selection function in accordance with one embodiment of the invention.
Figure 5:
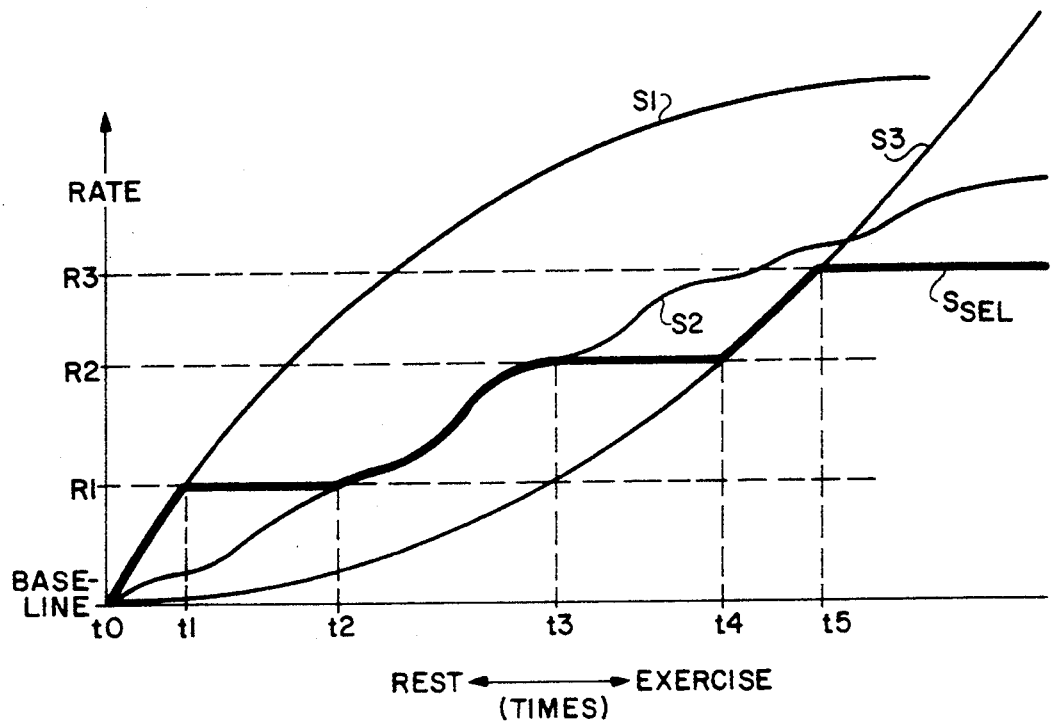
FIG. 5 shows a plot of the sensor indicated rate (SIR) signal as a function of time that results using the threshold and logic circuitry of FIG. 4.

A representative selection and threshold circuit 110 is further illustrated in connection with FIGS. 4 and 5. FIG. 4 shows a schematic diagram of a particular threshold and logic circuitry 110 that performs the function of the multiplexer 104 and threshold selection circuitry 106 of the selection circuitry 71. FIG. 5 shows a plot of the rate signal selected by the circuit of FIG. 4, i.e., the sensor indicated rate (SIR) signal, as a function of time. As seen in FIG. 4, three sensor signals, S1, S2 and S3 are generated by each of three sensors 112, 113 and 114, respectively. In turn, each of the signals S1, S2 and S3 is compared to a respective reference threshold signal R1, R2 and R3 in comparator circuits 116, 117 and 118. The comparator circuits 116, 117 and 118 are minimum comparator circuits, meaning that the output of each is equal to the lesser of the signals applied to its input terminals, i.e., the signal having the minimum amplitude. Stated another way, the output signal, M1, of comparator circuit 116 is equal to M1 = MIN(S1 or R1)

where "MIN" means the minimum value. Similarly, the output signal, M2, of comparator circuit 117 is equal to M2 = MIN(S2 or R2).

Likewise, the output signal, M3, of comparator circuit 118 is equal to

M3 = MIN(S3 or R3).

One of the three minimum signals, M1, M2 or M3, will be selected as the SIR signal. Hence, each of the signals M1, M2 and M3 may be considered as a "potential SIR" (PSIR) signal. The PSIR signals, M1, M2 and M3, are each applied as one of the inputs to a maximum threshold circuit 120. The output signal of the maximum threshold circuit 120, which output signal comprises the selected sensor signal, or SIR, is equal to the greater of the signals applied to its input terminals, i.e., the signal having the maximum amplitude. Stated another way, the output signal, $S_{SEL}$, of the comparator circuit 120 is equal to $S_{SEL}$ = MAX(M1 or M2 or M3)

where MAX means the maximum value.

Thus, as seen in FIG. 4, the selection circuitry 110 selects the sensor signal to be the greater of: (1) the lesser of S1 or R1; (2) the lesser of S2 or R2; or (3) the lesser of S3 or R3. Such selection is graphically depicted in FIG. 5 for exemplary variations of the sensor signals S1, S2 and S3 as a function of time. As seen in FIG. 5, the sensor signal S1 starts at a baseline rate and increases with increasing exercise (physical activity), with the greatest increase occurring at the onset of the exercise. The sensor signal S2 also starts at a baseline rate and also increases with increasing exercise, but has more or less the same slope throughout the increase. The sensor signal S3 likewise starts at a baseline rate and likewise increases with increasing exercise, with the least increase occurring at the onset of exercise. The three threshold reference signals, R1, R2 and R3, comprise fixed rate signals, with R1 being less than R2, and R2 being less than R3. Thus, at the initial onset of exercise, all three sensor signals are less than the reference threshold signals, so the comparator 116 selects S1, the comparator 117 selects S2, and the comparator 118 selects S3. Of these three selected signals, the sensor signal S1 is initially (at the onset of exercise) the greatest. Hence, the selected sensor signal, $S_{SEL}$, at the onset of exercise, is initially the sensor signal S1, as shown in FIG. 5 by the heavy line between the times t0 and t1.

Still referring to FIG. 5, as soon as the sensor signal S1 exceeds the threshold reference signal R1, then the comparator circuit 116 selects R1, instead of S1. Between the times t1 and t2, the signal R1 remains the greatest signal compared to the signals S2 and S3. Hence, the selected signal, $S_{SEL}$, between the times t1 and t2 as exercise increases is the threshold reference signal R1.

At time t2, the sensor signal S2 becomes greater than the threshold reference signal R1. Hence, at time t2, the comparator circuit 120 selects S2 as its output signal instead of the signal R1. This selection continues until S2 is no longer less than the threshold reference signal R2, which occurs at time t3. Thus, the selected signal, $S_{SEL}$, between the times t2 and t3 is the sensor signal S2.

At time t3, the comparator circuit 117 selects R2 as the minimum signal rather than S2. This selected signal R2 is still the maximum signal applied to the comparator circuit 120, so it remains selected as the selected sensor signal, $S_{SEL}$, until time t4, when the sensor signal S3 becomes greater than R2. Hence, the selected signal, $S_{SEL}$, between the times t3 and t4 is the threshold reference signal R2.

At time t4, the comparator circuit 118 still selects S3 as the minimum signal of the two signals S3 and R3. However, at this time, S3 becomes greater than either R1 or R2, the other two signals applied to the comparator circuit 120. Thus, the comparator circuit 120 selects S3 as the selected signal, $S_{SEL}$, after time t4.

At time t5, the sensor signal S3 becomes greater than the threshold reference signal R3. Hence, at time t5, the signal R3 is selected by the comparator 118, as well as the comparator 120. Thus, the selected signal, $S_{SEL}$, after time t5, is the threshold reference signal R3.

Hence, as graphically depicted in FIG. 5, the selection circuitry 110 shown in FIG. 4 applies a specific selection criteria in order to select one of a plurality of possible sensor signals that is:

$$S_{SEL} = MAX[MIN(S1,R1), MIN(S2,R2), MIN(S3,R3)]$$

where for notation purposes:
MAX[A,B,C] = largest of A and B and C; and
MIN(A,B) = smallest of A and B.

The selected signal, $S_{SEL}$, thus becomes the sensor indicated rate (SIR) signal.

In a preferred embodiment of the present invention, two physiological sensors are employed by the rate-responsive pacemaker: (1) an activity sensor, and (2) an oxygen saturation sensor. The activity sensor generates a sensor signal that provides an indication of what the pacing rate of the pacemaker should be based on the sensed activity of the patient. This signal, for purposes of the present invention, is referred to as the "activity indicated rate" (AIR) signal. The oxygen saturation sensor similarly generates a sensor signal that provides an indication of what the pacing rate of the pacemaker should be based on the sensed oxygen saturation in the patient's blood. The manner of sensing oxygen saturation is disclosed, e.g., in U.S. Pat. No. 4,815,469, incorporated herein by reference. The signal generated by the oxygen saturation sensor for purposes of the present invention, is referred to as the "oxygen saturation indicated rate" (OIR) signal.

The rate-responsive pacemaker of the preferred embodiment of the present invention further utilizes various programmed pacing limits or reference rates. One such rate is the pacemaker's "base rate" (BR). The base rate is the minimum rate at which the pacemaker will provide stimulation pulses on demand and is usually a fixed programmed value of between 60 and 70 ppm. Another rate used by the pacemaker is the "maximum sensor rate" (MSR). The MSR is a programmed value that represents the highest sensor rate signal that will be recognized by the pacemaker circuits.

In accordance with the present invention, the sensor selection circuitry of the preferred rate-responsive pacemaker uses the BR and MSR signals, as well as the sensed OIR and AIR signals, to generate a sensor indicated rate (SIR) signal that controls the rate at which pacing pulses are provided by the pacemaker. The manner in which the SIR signal is generated is best described as shown in FIG. 6. FIG. 6 plots the SIR signal as a function of time, showing the selection criteria that is used to determine the SIR signal.

Representative variations of the AIR signal (obtained from the activity sensor) and the OIR signal (obtained from the oxygen saturation sensor) are shown in FIG. 6 as a function of increased exercise (time) as the curves 140 and 142, respectively. Also shown in FIG. 6 are the MSR signal, shown as the thin horizontal line 138 near the top of FIG. 6 and the base rate (BR) signal, shown as the thin horizontal line 136 at the bottom of FIG. 6. In order to determine the SIR signal, shown as the heavy line or curve 144 in FIG. 6, a maximum oxygen saturation indicated rate (MOR) signal and a maximum activity indicated rate (MAR) signal are computed. The MOR signal is computed as the AIR signal plus a fixed integer n. In the preferred embodiment, n is an integer greater than 20, e.g., 30. Thus, MOR = AIR + 30. The MOR signal is shown in FIG. 6 as the dotted line curve 146.

The MAR signal is computed as the OIR signal plus a variable y, i.e., MAR = OIR + y. The variable y is equal to the ratio of the difference between the MSR signal and the OIR signal, and the difference between the MSR signal and the BR signal, which ratio is multiplied by a prescribed multiplication factor, m. Stated another way, $$MAR = OIR + m[(MSR-OIR)/(MSR-BR)].$$

The multiplication factor m is an integer greater than 20, e.g., m=30. Thus, the maximum activity indicated rate (MAR) signal may be expressed as:

$$MAR = OIR + 30[(MSR-OIR)/(MSR-BR)].$$

The MAR signal is shown in FIG. 6 as the thin dashed line 148. As seen in FIG. 6, as the OIR signal approaches the maximum sensor rate (MSR) signal as increased exercise persists (i.e., after a latency time period), the MAR signal merges into the OIR signal.

The SIR signal, in accordance with the selection criteria shown in FIG. 6, is determined as the minimum value of: (1) the maximum sensor rate (MSR) signal; (2) the largest of the oxygen saturation or activity rate (OIR or AIR) signals; (3) the maximum oxygen saturation indicated rate (MOR) signal; or (4) the maximum activity indicated rate (MAR) signal. This selection criteria may be expressed as:

$$SIR = MIN\{MSR, MAX(OIR, AIR), MOR, MAR\};$$

or $$SIR = MIN\{MSR, MAX(OIR,AIR), (AIR+30), [OIR+30(MSR-OIR)/(MSR-BR)]\}.$$

Advantageously, using the selection criteria expressed above or as shown in FIG. 6, the SIR signal is weighted so as to favor the activity signal during the initial onset of exercise or increasing exercise, while favoring the oxygen saturation signal after exercise has stabilized or in the absence of exercise. Thus, the latency of the more physiologic oxygen saturation sensor signal controls the pacing rate after the latency associated with such oxygen saturation sensor signal has elapsed.

Those of skill in the art will recognize that implementation of the selection criteria depicted in FIG. 6 can be achieved either in hardware circuitry similar to that shown in FIG. 3 or 4, and/or in software circuitry, used, e.g., as part of one of the signal conditioners shown in FIG. 3, or as part of the sensor signal processing elements shown in the aforecited patents and patent application. Indeed, one of the advantages of the present invention is the ease with which it may be implemented in a wide variety of configurations, using a wide variety of circuit and processing elements.

It is thus seen from the above description that a more hemodynamically beneficial pacing rate is achieved in a rate-responsive pacemaker by using a dynamically adjusted weighted combination of a plurality of sensor signals to determine the sensor indicated rate (SIR) signal of the pacemaker. Such hemodynamically beneficial pacing rate is achieved by heavily weighting the particular sensor signal that best typifies the physiologic need of the patient at a given time. Advantageously, such dynamic weighting is achieved simply and inexpensively by comparing the magnitude of the various sensor signals to each other and to preselected reference threshold values using readily available threshold comparator circuits or program elements that sense minimum and maximum signal values.

It is further seen from the above description that the present invention provides a multi-sensor rate-responsive pacemaker using both an oxygen saturation sensor (to measure the oxygen saturation level of the patient's blood) and an activity sensor (to measure the physical activity level of the patient), wherein an SIR signal for such pacemaker is a weighted combination of the oxygen saturation sensor signal and the activity sensor signal, with the activity sensor signal being heavily weighted during the initial onset or acceleration of increased physical activity (e.g., exercise), and with the oxygen saturation sensor signal being heavily weighted at other times (e.g., rest, stable physical activity, or return to rest).

It is also seen from the above description that one embodiment of the invention provides a multi-sensor rate-responsive pacemaker using both an oxygen saturation sensor and an activity sensor wherein one of: (a) the oxygen saturation sensor signal; (b) the activity sensor signal; (c) a predetermined (e.g., programmed) maximum sensor rate (MSR) signal; (d) a maximum oxygen saturation sensor rate (MOR) signal derived from the activity sensor signal; or (e) a maximum activity sensor rate (MAR) signal derived from the oxygen saturation sensor signal and other rate limits, is selected as the SIR signal of the pacemaker. Specifically, for a preferred configuration, it is seen that the SIR signal is selected to be lesser of: (i) the MSR signal; (ii) the largest of the activity sensor signal or the oxygen saturation signal; (iii) the MOR signal; or (iv) the MAR signal.

While the invention herein disclosed has been described by means of specific embodiments and applications thereof, numerous modifications and variations could be made thereto by those skilled in the art without departing from the scope of the invention set forth in the claims.

What is claimed is:

1. An implantable rate-responsive pacemaker comprising:

a plurality of sensors, each sensor being adapted to sense a physiologic-related parameter of a patient and to generate a sensor signal indicative of such sensed physiologic-related parameter;

a sense amplifier that senses natural contractions of the patient's heart;

a pulse generator that generates stimulation pulses responsive to a pacing signal, each stimulation pulse having a pacing energy sufficient to cause a contraction of a preselected chamber of the patient's heart;

timing circuitry that defines an escape time interval;

control logic circuitry coupled to said sense amplifier, and said timing circuitry that starts said escape time interval at the beginning of a sensed or paced cardiac cycle, and said control logic circuitry further coupled to said pulse generator generates said pacing signal at the end of said escape time interval unless a natural contraction of the patient's heart is sensed by the sense amplifier prior to the end of the escape interval, in which case the escape time interval is restarted and no pacing signal is generated;

processing means coupled to said timing circuitry and said plurality of sensors for generating a sensor indicated rate (SIR) signal comprising selection means for respectively comparing each of said plurality of sensor signals against a predetermined threshold signal, and for selecting the smallest of said sensor signal or said predetermined threshold signal as a potential sensor indicated rate (PSIR) signal, thereby generating a plurality of PSIR signals; and for selecting said SIR signal as either of the largest and smallest of said plurality of PSIR signals, said SIR signal being used by said timing means to define the duration of said escape time interval.

2. The rate-responsive pacemaker, as set forth in claim 1, wherein said plurality of sensors comprise:
an oxygen saturation sensor for sensing the oxygen saturation level of the patient's blood;
and an activity sensor for sensing the physical activity of the patient.

3. The rate-responsive pacemaker, as set forth in claim 2, wherein said pacemaker has a base rate (BR) and a maximum sensor rate (MSR) programmed therein for use by said processing means, and wherein said oxygen saturation sensor generates an oxygen saturation indicated rate (OIR) signal, and said activity sensor generates an activity indicated rate (AIR) signal; and wherein said processing means generates a maximum oxygen saturation indicated rate (MOR) signal that comprises the AIR signal plus n, where n is an integer greater than 20, and a maximum activity indicated rate (MAR) signal equal to:

$$MAR = OIR + m[(MSR-OIR)/(MSR-BR)],$$

where m is also an integer greater than 20; and wherein said sensor indicated rate (SIR) signal is equal to the minimum of: (1) said MSR signal, (2) the maximum of said OIR or AIR signals, (3) said MOR signal, or (4) said MAR signal.

4. An implantable rate-responsive pacemaker comprising:
a plurality of sensors, each being adapted to sense a physiologic-related parameter of a patient and to generate a sensor signal indicative of such sensed physiologic-related parameter;
a sense amplifier that senses natural contractions of the patient's heart;
a pulse generator that generates stimulation pulses responsive to a pacing signal, each stimulation pulse having a pacing energy sufficient to cause contraction of a selected chamber of the patient's heart;
timing circuitry that defines an escape time interval;
control logic circuitry coupled to said sense amplifier, and said timing circuitry that starts said escape time interval at the beginning of a sensed or paced cardiac cycle, and said control logic circuitry further coupled to said pulse generator generates said pacing signal at the end of said escape time interval unless a natural contraction of the patient's heart is sensed by the sense amplifier prior to the end of the escape interval, in which case the escape time interval is restarted and no pacing signal is generated;
processing means coupled to said timing circuitry and said plurality of sensors for generating a sensor indicated rate (SIR) signal, as a prescribed weighted combination of the plurality of sensor signals, with the amount of weight given one sensor signal at any given time varying as a function of which sensor signal best typifies the physiologic need of the patient at that time, said SIR signal being used by said timing means to define the duration of said escape time interval; and
said processing means further comprises:
signal conditioning means for conditioning a predetermined group of said sensor signals to produce at least one conditioned sensor signal; and
selection means for selecting one of said plurality of sensor signals, said at least one conditioned sensor signal, or one of a plurality of reference threshold signals, as a potential sensor indicated rate (PSIR) signal, depending upon which is smallest, and for selecting said PSIR signal as the SIR signal whenever it satisfies a specified criteria.

5. The rate-responsive pacemaker, as set forth in claim 4, wherein said selection means selects a plurality of PSIR signals, and wherein the largest of said PSIR signals is selected as the SIR signal.

6. An implantable rate-responsive pacing system comprising:
a plurality of sensors, each being adapted to sense a respective physiologic-related parameter of a patient and to generate a physiological signal indicative of such sensed physiologic-related parameter;
a sense amplifier that senses natural contractions of the patient's heart;
a pulse generator that generates stimulation pulses responsive to a pacing signal and delivers such stimulation pulses to the patient's heart;
control/timing means for defining an escape interval and starting said escape interval at the beginning of a sensed or paced cardiac cycle, and generating said pacing signal at the end of said escape interval unless a natural contraction of the patient's heart is sensed by the sense amplifier prior to the conclusion of the escape interval, in which case the escape interval is restarted and no pacing signal is generated;
telemetry means for programming said pacemaker with a desired base rate (BR) signal and a maximum sensor rate (MSR) signal; and
sensor processing means coupled to said control/timing means for generating a sensor indicated rate (SIR) signal, said SIR signal being used by said control/timing means to define the duration of said escape interval, said SIR signal comprising the lesser of: (a) the MSR signal; or (b) the largest of said plurality of physiological signals;
whereby said rate-responsive pacing system generates stimulation pulses on demand at a rate determined by the SIR signal.

7. The rate-responsive pacing system, as set forth in claim 6, wherein said sensor processing means is for further computing a first maximum sensor rate ($MR_1$) for a first sensor of said plurality of sensors and a second maximum sensor rate ($MR_2$) for a second of said plurality of physiological sensors; and wherein said SIR signal comprises the lesser of: (a) the MSR signal; (b) the largest of said plurality of rate signals; (c) the $MR_1$ signal; or (d) the $MR_2$ signal.

8. The rate-responsive pacing system of claim 7, wherein said $MR_1$ signal comprises the sum of the physiological signal generated by the second sensor and a fixed integer value n.

9. The rate-responsive pacing system of claim 7, wherein said $MR_2$ signal comprises the sum of the physiological signal generated by the first physiological sensor and a variable y, said variable y comprising a function of the difference between the physiological signal of the first physiological sensor and the MSR signal.

10. The rate-responsive pacing system of claim 9, wherein the variable y comprises $y = m[(MSR-x)/(MSR-BR)]$, where m is an integer greater than 20, and x is the rate signal of the first physiological sensor.

11. The rate-responsive pacing system of claim 10, wherein said first physiological sensor comprises a sensor that senses the oxygen saturation content of the patient's blood, and said second physiological sensor comprises a sensor that senses the physical activity of the patient.

12. The rate-responsive pacing system of claim 11, wherein m is equal to 30.

13. A method of operating an implantable rate-responsive pacemaker that utilizes a plurality of rate sensors, each of said rate sensors generating a respective rate signal that indicates a sensed physiologic-related parameter of a patient, said method comprising the steps of:
   (a) processing said plurality of rate signals to determine a sensor indicated rate (SIR) signal, said processing including:
      (1) defining a maximum sensor rate (MSR) signal;
      (2) selecting the SIR signal as the lesser of: (i) the MSR signal, or (ii) the largest of said plurality of rate signals;
   (b) using said SIR signal to define an escape interval for said implantable rate-responsive pacemaker;
   (c) sensing natural cardiac activity of the patient;
   (d) starting said escape interval upon sensing natural cardiac activity; and
   (e) generating a stimulation pulse at the end of said escape interval and restarting said escape interval unless a natural contraction of the patient's heart is sensed prior to the end of the escape interval, in which case the escape interval is immediately restarted and no stimulation signal is generated;

whereby said rate-responsive pacemaker generates stimulation pulses on demand at a rate determined by the SIR signal, said SIR signal resulting from the specified processing of the plurality of rate signals obtained from the plurality of rate sensors.

14. The method of claim 13, wherein step (a) further includes:
   computing a first maximum sensor rate ($MR_1$) for a first sensor of said plurality of sensors and a second maximum sensor rate ($MR_2$) for a second of said plurality of sensors; and
   selecting the SIR signal as the lesser of: (i) the MSR signal, (ii) the largest of said plurality of rate signals, (iii) the $MR_1$ signal, or (iv) the $MR_2$ signal.

15. The method of claim 14, wherein the step of computing the $MR_1$ signal comprises adding a fixed increment n to the rate signal of the second sensor.

16. The method of claim 14, wherein the step of computing the $MR_2$ signal comprises adding a variable y to the rate signal of the first sensor.

17. The method of claim 16, wherein the variable y comprises $y = m[(MSR-x)/(MSR-BR)]$, where m is an integer greater than 20, x is the rate signal of the first sensor, and BR is a base rate of the rate-responsive pacemaker.

* * * * *